US009592352B2

(12) United States Patent
Matsuzawa

(10) Patent No.: US 9,592,352 B2
(45) Date of Patent: Mar. 14, 2017

(54) ULTRASOUND-GUIDED PIERCING NEEDLE AND INDWELLING NEEDLE

(75) Inventor: Masaki Matsuzawa, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 777 days.

(21) Appl. No.: 13/515,403

(22) PCT Filed: Nov. 1, 2010

(86) PCT No.: PCT/JP2010/069401
§ 371 (c)(1),
(2), (4) Date: Jun. 12, 2012

(87) PCT Pub. No.: WO2011/077837
PCT Pub. Date: Jun. 30, 2011

(65) Prior Publication Data
US 2012/0253297 A1    Oct. 4, 2012

(30) Foreign Application Priority Data

Dec. 21, 2009    (JP) .................................. 2009-289598

(51) Int. Cl.
*A61M 5/32*    (2006.01)
*A61M 5/158*    (2006.01)
(Continued)

(52) U.S. Cl.
CPC ............ *A61M 5/329* (2013.01); *A61M 5/158* (2013.01); *A61B 8/0841* (2013.01); *A61B 2017/3413* (2013.01); *A61B 2090/3925* (2016.02)

(58) Field of Classification Search
CPC ........ A61B 2019/5425; A61B 17/3403; A61B 2017/3413; A61B 8/0841; A61B 18/1477;
(Continued)

(56) References Cited

U.S. PATENT DOCUMENTS 4,401,124 A * 8/1983 Guess et al. .................. 600/458
4,582,061 A * 4/1986 Fry ...................... A61B 8/0833
600/431
(Continued)

FOREIGN PATENT DOCUMENTS

DE    20 2005 008 489 U1    10/2005
EP        0 072 671 A2      2/1983
(Continued)

OTHER PUBLICATIONS

Extended Search Report issued by the European Patent Office on May 6, 2013, in the corresponding European Patent Application No. 10839073.3. (5 pages).
(Continued)

*Primary Examiner* — Bradley Osinski
(74) *Attorney, Agent, or Firm* — Buchanan, Ingersoll & Rooney PC

(57) ABSTRACT

An ultrasound-guided piercing needle constituting the internal needle of an indwelling needle has ridged and grooved portions which reflect ultrasonic waves. The ridged and grooved portions comprise grooves, which are disposed on the outer periphery near the tip having a blade face, and ridges, which are arranged on both sides of the grooves.

19 Claims, 9 Drawing Sheets

(51) Int. Cl.
*A61B 8/08* (2006.01)
*A61B 17/34* (2006.01)

(58) Field of Classification Search
CPC ........ A61B 2090/3925; A61F 9/00745; A61M 5/329; A61M 5/158
See application file for complete search history.

(56) References Cited

U.S. PATENT DOCUMENTS

| | | | |
|---|---|---|---|
| 5,490,521 A * | 2/1996 | Davis ................... | A61B 8/0833 600/458 |
| 7,682,337 B2 * | 3/2010 | Valaie ...................... | 604/164.01 |
| 2004/0249288 A1 | 12/2004 | Ichikawa | |
| 2006/0047254 A1 * | 3/2006 | Akahoshi ...................... | 604/272 |
| 2009/0137906 A1 | 5/2009 | Maruyama et al. | |
| 2010/0168684 A1 | 7/2010 | Ryan | |

FOREIGN PATENT DOCUMENTS

| | | |
|---|---|---|
| EP | 1 426 011 A1 | 6/2004 |
| EP | 1 908 406 A1 | 4/2008 |
| FR | 2 272 633 A1 | 12/1975 |
| JP | 3-228748 A | 10/1991 |
| JP | 10-248793 A | 9/1998 |
| JP | 3171525 B2 | 5/2001 |
| JP | 3890013 B2 | 3/2007 |
| JP | 2009-233007 A | 10/2009 |
| WO | WO 2007/013130 A1 | 2/2007 |

OTHER PUBLICATIONS

International Search Report (PCT/ISA/210) issued on Feb. 15, 2011, by the Japanese Patent Office as the International Searching Authority for International Application No. PCT/JP2010/069401.
Written Opinion (PCT/ISA/237) issued on Feb. 15, 2011, by the Japanese Patent Office as the International Searching Authority for International Application No. PCT/JP2010/069401.
Office Action/Search Report dated Feb. 2, 2015, issued by the Chinese Patent Office in corresponding Chinese Patent Application No. 201080046771.4 and an English translation of Office Action/Search Report. (9 pages).

* cited by examiner

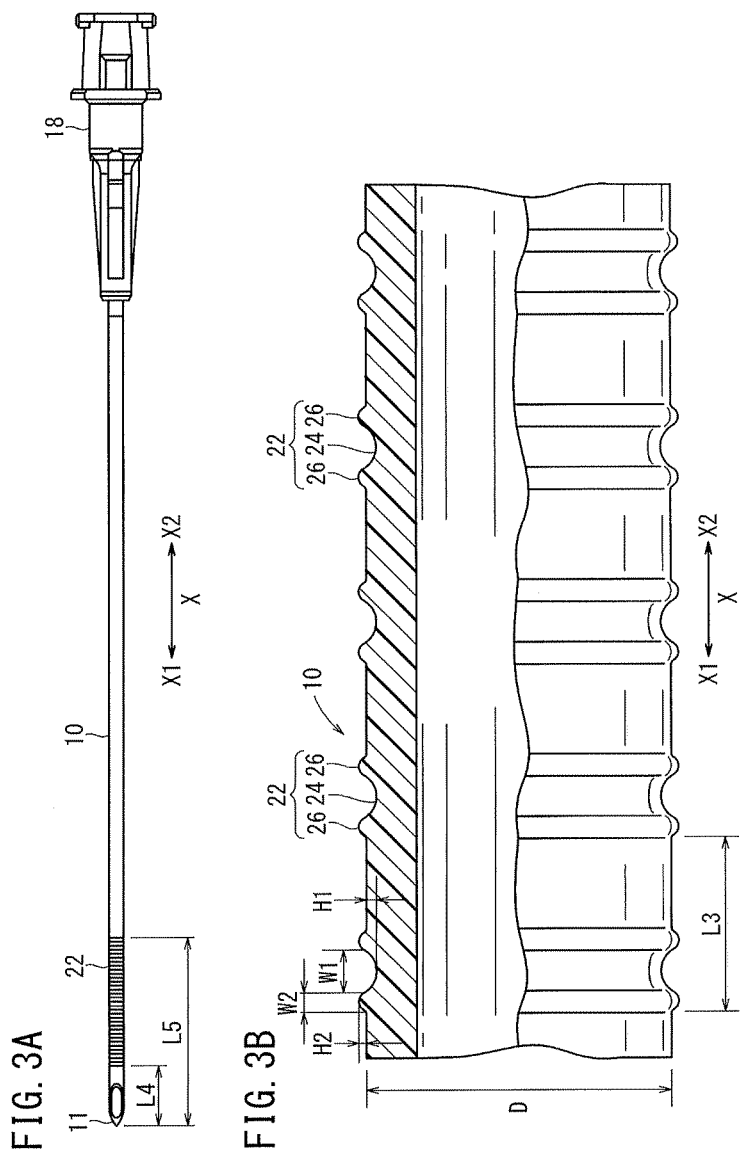

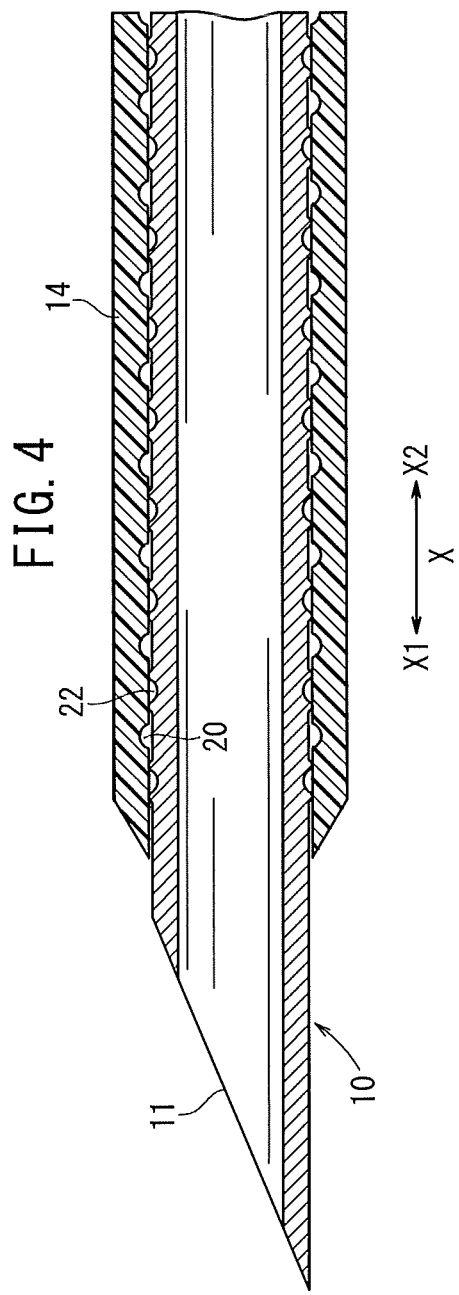

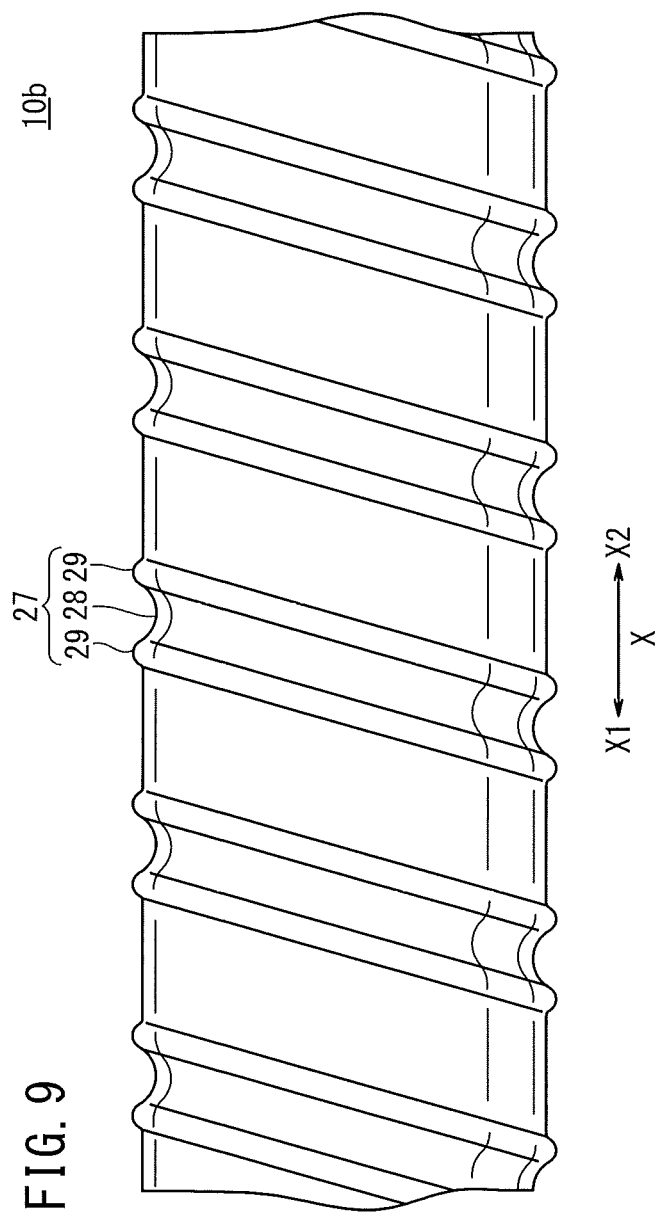

ULTRASOUND-GUIDED PIERCING NEEDLE AND INDWELLING NEEDLE

TECHNICAL FIELD

The present invention relates to an ultrasound-guided piercing needle for piercing a patient while detecting a position of the piercing needle utilizing the reflection of ultrasonic waves, as well as to an indwelling needle incorporating the piercing needle.

BACKGROUND ART

For example, at the time of transfusion of a high-concentration pabulum into a patient, an indwelling needle including a catheter (outer needle) and a piercing needle (inner needle) is made to pierce the patient, the piercing needle is evulsed with the catheter left in a pierced state, a guide wire is inserted through the catheter to reach a blood vessel (vein) near the heart, the catheter is evulsed, a central arterial catheter is inserted along the guide wire into the blood vessel, the guide wire is removed so that only the central arterial catheter is left indwelling in the pierced state, a transfusion line through which a pabulum, a medicinal liquid, or the like is supplied is connected to the central arterial catheter, and a transfusion is conducted.

In the case that such an indwelling needle is made to pierce a blood vessel, for example, ultrasonic waves are emitted from an ultrasonic imaging device, thereby confirming the position of the blood vessel to be pierced. In addition, the piercing needle, which is in the pierced state, is irradiated with ultrasonic waves, and a surgical procedure is carried out while confirming the position of the piercing needle through an image obtained based on the reflected waves.

Hitherto, as such an indwelling needle, indwelling needles in which an outer circumferential surface of a piercing needle (inner needle) is provided with a helical groove or a V-shaped groove in a recessed form have been known (see, for example, Japanese Patent No. 3171525 and Japanese Laid-Open Patent Publication No. 03-228748). Upon using this type of indwelling needle, the piercing needle is made to pierce a diseased part of a patient, the pierced part is irradiated with ultrasonic waves emitted from an ultrasonic imaging device, whereupon the ultrasonic waves are reflected by an air layer in the helical groove or the V groove, and the reflected waves are received by the ultrasonic imaging device in order to obtain a picked-up image (echo image) of the piercing needle.

SUMMARY OF INVENTION

Meanwhile, in order to accurately grasp the position of the piercing needle, as mentioned above, it is important to obtain a clear echo image. In order to obtain a clear echo image, reflected waves with sufficient intensity must be returned from the piercing needle to a probe of the ultrasonic imaging device. Therefore, it is desired to develop an ultrasound-guided piercing needle, which ensures that stronger reflected waves, and hence a clearer echo image, can be obtained.

The present invention has been made in consideration of the above-mentioned problems. Accordingly, it is an object of the present invention to provide an ultrasound-guided piercing needle and an indwelling needle, which ensure that ultrasonic waves can be reflected more effectively, whereby the position of the piercing needle in a living body can be confirmed assuredly and with high accuracy.

According to the present invention, there is provided an ultrasound-guided piercing needle having a ridged and grooved portion, which reflects ultrasonic waves, the ridged and grooved portion comprising a grooved portion provided on an outer circumferential surface near a distal portion having a blade face, and ridged portions provided on both sides of the grooved portion.

In this manner, since the ridged and grooved portion includes the grooved portion and the ridged portions provided on both sides of the grooved portion, ultrasonic waves are reflected not only by the grooved portion, but also by the ridged portions. Therefore, ultrasonic waves can be reflected assuredly and suitably, and can be detected by the ultrasonic imaging device. Consequently, upon piercing a patient, the ultrasound-guided piercing needle can be confirmed assuredly and with high accuracy by the ultrasonic imaging device, whereby a safe and assured procedure can be carried out while confirming the position of the ultrasound-guided piercing needle.

In addition, in the aforementioned ultrasound-guided piercing needle, the ridged and grooved portion may be formed in an annular shape on the outer circumferential surface, and a plurality of ridged and grooved portions may be provided along an axial direction of the ultrasound-guided piercing needle.

With such a configuration, the formation of the ridged and grooved portion in an annular form on the outer circumferential surface enables the entire circumference to act as a reflecting surface, so that when piercing is carried out, ultrasonic waves can be reflected effectively, irrespective of the position around the axis of the ultrasound-guided piercing needle. In addition, since plural ridged and grooved portions are provided along the axial direction of the ultrasound-guided piercing needle, the number of parts that provide suitable reflection of ultrasonic waves is increased significantly. Therefore, ultrasonic waves can be reflected effectively, and more sufficient reflected waves can be obtained. Consequently, the position of the ultrasound-guided piercing needle by the ultrasonic imaging device can be confirmed with higher accuracy.

Further, in the aforementioned ultrasound-guided piercing needle, the plurality of ridged and grooved portions may be formed such that the ridged portions of adjacent ones of the ridged and grooved portions are continuous with each other.

By forming the ridged and grooved portions continuously along the axial direction of the ultrasound-guided piercing needle, ultrasonic waves can be reflected more effectively, and more sufficient reflected waves can be obtained. As a result, the position of the ultrasound-guided piercing needle by the ultrasonic imaging device can be confirmed with higher accuracy.

In addition, in the aforementioned ultrasound-guided piercing needle, the ridged and grooved portion may be formed in a helical shape extending around the outer circumferential surface at least a plurality of times.

By forming the ridged and grooved portion in this manner, the entire circumference acts as a reflecting surface, so that when piercing is carried out, ultrasonic waves can be reflected effectively, irrespective of the position around the axis of the ultrasound-guided piercing needle. In addition, the number of parts provided for suitable reflection of ultrasonic waves is increased, so that more sufficient reflected waves can be obtained. Consequently, the position of the ultrasound-guided piercing needle by the ultrasonic imaging device can be confirmed with higher accuracy.

Further, in the aforementioned ultrasound-guided piercing needle, the grooved portion may be arcuate in cross section.

According to the above configuration, an inner wall surface of the grooved portion constitutes an arcuate reflecting surface. Thus, even if the piercing angle changes, ultrasonic waves incident on the grooved portion can be reflected in substantially the same direction as the direction of incidence. Therefore, ultrasonic waves can be reflected suitably, and as a result, the position of the ultrasound-guided piercing needle by the ultrasonic imaging device can be confirmed with higher accuracy.

In addition, in the aforementioned ultrasound-guided piercing needle, the ridged portions may be arcuate in cross section.

According to the above configuration, outer wall surfaces of the ridged portions constitute arcuate reflecting surfaces. Thus, even if the piercing angle changes, ultrasonic waves incident on the ridged portions can be reflected in substantially the same direction as the direction of incidence. Therefore, ultrasonic waves can be reflected suitably, and as a result, the position of the ultrasound-guided piercing needle by the ultrasonic imaging device can be confirmed with higher accuracy.

Further, according to the present invention, there is provided an indwelling needle including an inner needle and an outer needle in which the inner needle is inserted, wherein the inner needle is configured as an ultrasound-guided piercing needle having a ridged and grooved portion, which reflects ultrasonic waves. The ridged and grooved portion further comprises a grooved portion provided on an outer circumferential surface near a distal portion having a blade face, and ridged portions provided on both sides of the grooved portion.

BRIEF DESCRIPTION OF DRAWINGS

FIG. 3A is a plan view showing the configuration of an ultrasound-guided piercing needle and an inner needle hub according to one embodiment of the present invention;

FIG. 3B is a enlarged side view, shown partially in cross section, of an ultrasound-guided piercing needle according to one embodiment of the present invention;

FIG. 4 is a partially omitted enlarged sectional view showing a part near a distal portion of an indwelling needle having an ultrasound-guided piercing needle according to one embodiment of the present invention;

FIG. 9 is an enlarged side view showing grooved portions of an ultrasound-guided piercing needle according to a second modification.

DESCRIPTION OF EMBODIMENTS

An ultrasound-guided piercing needle and an indwelling needle according to the present invention will be described in relation to preferred embodiments with reference to the attached drawings.

Figure 1:
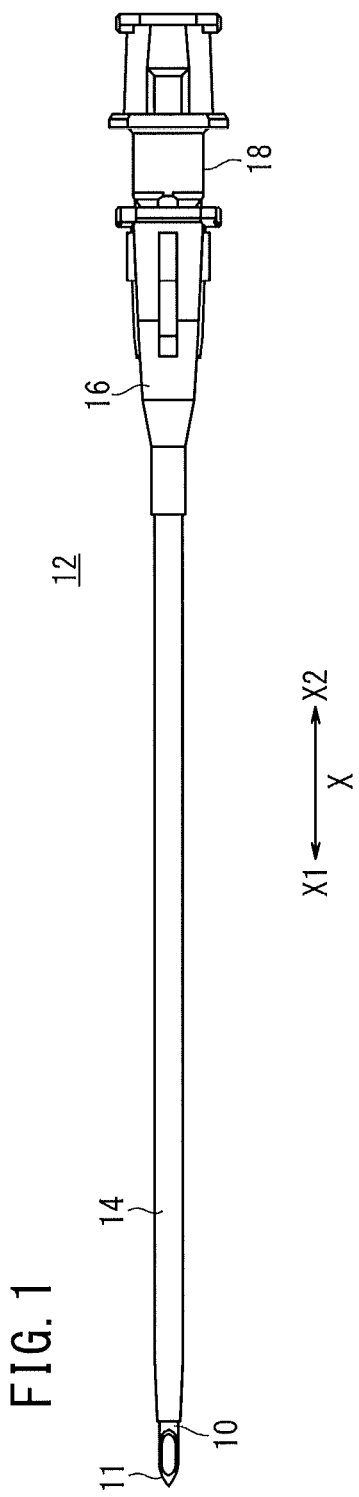
FIG. 1 is an overall view showing the configuration of an indwelling needle having an ultrasound-guided piercing needle according to one embodiment of the present invention.

FIG. 1 is an overall view showing a configuration of an indwelling needle 12 having an ultrasound-guided piercing needle 10 (hereinafter referred to simply as a "piercing needle") according to an embodiment of the present invention. Incidentally, for convenience of description, in each of the attached drawings (exclusive of some drawings), the axial direction of the indwelling needle 12 and the axial direction of each of members constituting the indwelling needle 12 are indicated by the arrow X. In addition, a direction toward distal portions of the indwelling needle 12 and members thereof is denoted by the arrow X1, whereas a direction toward proximal portions of the members is denoted by the arrow X2.

As shown in FIG. 1, the indwelling needle 12 according to one configuration example includes a catheter 14, an outer needle hub 16 connected to a proximal portion of the catheter 14, a piercing needle 10 inserted into the interior of the catheter 14, and an inner needle hub 18 connected to a proximal portion of the piercing needle 10.

The inner needle hub 18 is configured to fit into the interior of the outer needle hub 16. In FIG. 1, a condition is shown in which a connected body of the piercing needle 10 and the inner needle hub 18 is fitted into a connected body of the catheter 14 and the outer needle hub 16. In this condition, a blade face 11, which is formed at a distal portion of the piercing needle 10, is exposed (protruded) from a distal end of the catheter 14. A syringe 30 can be connected to a proximal portion of the inner needle hub 18 (see FIG. 5).

Figure 2A:
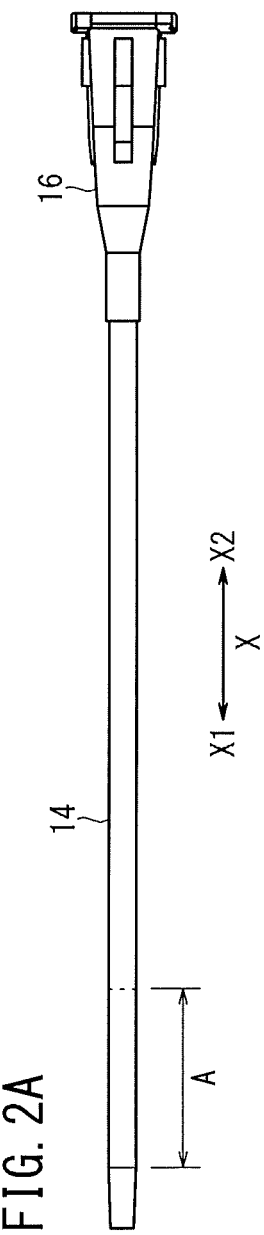
FIG. 2A is a plan view showing the configuration of a catheter and an outer needle hub shown in FIG. 1.

FIG. 2A is a plan view showing a configuration of the catheter 14 and the outer needle hub 16 of the indwelling needle 12 shown in FIG. 1. In the indwelling needle 12 according to one exemplary configuration, the catheter 14 constitutes an outer needle, which is formed, for example, from a transparent resin material. The catheter 14 has an appropriate degree of elasticity and is formed in a tubular shape so as to surround the piercing needle 10. The catheter 14 reaches the vicinity of the distal end of the piercing needle 10. When the distal end of the piercing needle 10 is inserted into a blood vessel, the catheter 14 also is inserted into the same blood vessel.

Examples of materials constituting the catheter 14 may include various flexible resins such as ethylene-tetrafluoro-ethylene copolymer (ETFE), polyurethane, and polyether nylon resin. Examples of materials constituting the outer needle hub 16 may include polyolefins such as polyethylene, polypropylene, ethylene-vinyl acetate copolymer, etc., polyvinyl chloride, polymethyl methacrylate, polycarbonates, polybutadiene, polyamides, and polyesters.

Figure 2B:
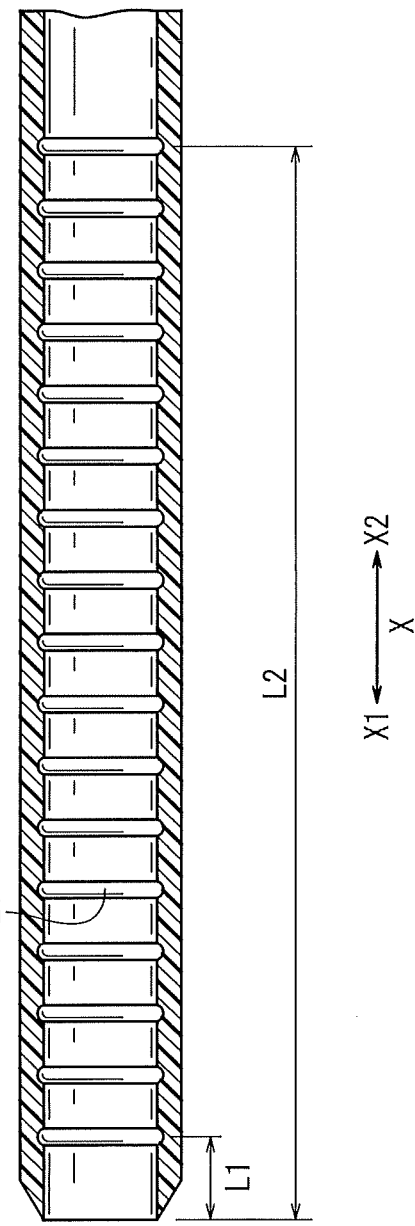
FIG. 2B is a partially omitted enlarged sectional view, taken along an axial direction, of a distal portion and portions in the vicinity thereof of the catheter shown in FIG. 2A.

FIG. 2B is a partially omitted enlarged sectional view, taken along the axial direction, of a distal portion and a portion in the vicinity thereof of the catheter 14. As shown in FIG. 2B, an inner circumferential surface proximate a distal portion of the catheter 14 is formed with inner circumferential grooved portions 20, which are hollowed in a shape protuberant to the outer circumferential side. In the example shown in the drawing, the inner circumferential grooved portions 20 are substantially semicircular in cross section, are formed in an annular shape with a substantially constant depth in the circumferential direction, and are formed at predetermined intervals in the axial direction and over a predetermined range (denoted by A in FIG. 2A).

The distance L1 from a maximal distal portion of the catheter 14 to the inner circumferential grooved portion 20 on the distal side thereof is set, for example, from 0 to 3 mm, and more preferably, from 1 to 2 mm. The distance L2 in the axial direction (X-direction) from the maximal distal portion of the catheter 14 to the inner circumferential grooved portion 20 on the proximal side thereof is set, for example, from 2 to 10 mm, and more preferably, from 6 to 8 mm. The depth in the radial direction of the inner circumferential grooved portion 20 is set, for example, from 10 to 25 µm. The groove pitch (the interval in the axial direction) of the plurality of inner circumferential grooved portions 20 is set, for example, from 0.2 to 0.5 mm.

Incidentally, the inner circumferential grooved portions 20 are not restricted to being formed as annular grooves, which are formed at an interval in the axial direction, but may comprise a groove, which extends helically in the axial direction. Further, the inner circumferential grooved portions 20 may be omitted.

FIG. 3A is a plan view showing a configuration of a piercing needle 10 and an inner needle hub 18 according to an embodiment of the present invention. In an indwelling needle 12 according to one exemplary configuration, the piercing needle 10 constitutes an inner needle. The piercing needle 10 comprises a hollow tube formed at a distal portion thereof with a blade face 11, which is inclined relative to the axis of the piercing needle 10.

The material constituting the piercing needle 10 is a material from which a sharp blade edge can be formed thereon to provide a sufficient piercing force (penetrating force), and which has strength necessary for piercing. Examples of suitable materials include stainless steel, aluminum alloys, and copper alloys.

A proximal portion of the piercing needle 10 is connected to and held by a distal portion of the inner needle hub 18. Examples of materials constituting the inner needle hub 18 include the same materials as those of the outer needle hub 16, as mentioned above. As shown in FIG. 3A, an outer circumferential surface in the vicinity of the distal portion of the piercing needle 10 (a predetermined range on the proximal side relative to the blade face 11) is formed with ridged and grooved portions 22, for reflecting ultrasonic waves over a predetermined range along the axial direction of the piercing needle 10.

FIG. 3B is an enlarged side view partially in cross section showing the ridged and grooved portions 22 of the piercing needle 10 shown in FIG. 3A. The outside diameter D of the piercing needle 10 is set, for example, from 0.7 to 0.8 mm. In the present embodiment, the ridged and grooved portions 22 are formed in an annular shape on the outer circumferential surface of the piercing needle 10. Plural ridged and grooved portions 22 are provided at intervals along the axial direction (X-direction) of the piercing needle 10. In the example shown in the drawing, the interval L3 of the ridged and grooved portions 22 in the axial direction may be set to a constant value. In this case, the interval L3 is set, for example, from 200 to 500 µm.

The distance L4 (see FIG. 3A) along the axial direction from a maximal distal portion of the piercing needle 10 to the ridged and grooved portion 22 on the distal side is set, for example, from 0.3 to 5 mm. The distance L5 (see FIG. 3A) along the axial direction from the maximal distal portion of the piercing needle 10 to the ridged and grooved portion 22 on the proximal side is set, for example, from 5 to 50 mm.

Incidentally, in the example of the piercing needle 10 shown in the drawing, the interval L3 of the ridged and grooved portions 22 in the axial direction is set to a constant value. However, some or all of the intervals of the plural ridged and grooved portions 22 may be set to a different value. For instance, the interval of the ridged and grooved portions 22 may be set to be smaller on the distal side of the piercing needle 10 (or the interval of the ridged and grooved portions 22 may be set to be greater on the proximal side of the piercing needle 10).

As shown in FIG. 3B, the ridged and grooved portion 22 includes the grooved portion 24, which is formed in an annular shape so as to protrude toward the inner circumferential side, and the ridged portions 26, which are disposed on both sides (both sides in the axial direction) of the grooved portion 24, and are formed in an annular shape so as to protrude toward the radially outer side.

In the present embodiment, the grooved portion 24 is arcuate in cross section, and is formed with a substantially constant depth over the circumferential direction. The width W1 of the grooved portion 24 in the axial direction is set, for example, from 30 to 100 µm. The depth H1 of the grooved portion 24 in the radial direction is set, for example, from 5 to 20 µm.

In the present embodiment, the ridged portion 26 is arcuate in cross section, and is formed with a substantially constant height over the circumferential direction. The width W2 of the ridged portion 26 in the axial direction is set, for example, from 5 to 20 µm. The height H2 of the ridged portion 26 in the radial direction is set, for example, from 1 to 15 µm. Thus, as clearly shown in FIG. 3B, the outer diameter of the ridged portion 26 is greater than the outside diameter D of the outer circumferential surface of the piercing needle 10.

Incidentally, the ridged and grooved portions 22, which are configured as described above, can be formed comparatively easily by subjecting a tubular blank material (work) to machining work, such as plastic working, cutting, and electric discharge machining.

FIG. 4 is a partially omitted enlarged sectional view showing a condition in which a piercing needle 10 according to one embodiment of the present invention is inserted into a catheter 14, such that a distal portion, inclusive of a blade face 11, of the piercing needle 10 is exposed (protruded) from a distal portion of the catheter 14. The inside diameter of the catheter 14 is set to be approximately equal to or slightly larger than the outside diameter of the ridged portions 26, so that the piercing needle 10, provided with the ridged portions 26 thereon, can be inserted into the catheter 14.

Further, as shown in FIG. 4, in the present embodiment, inner circumferential grooved portions 20 and ridged and grooved portions 22 of the catheter 14 and the piercing needle 10 are formed such that, in a condition in which the distal portion of the piercing needle 10 is exposed (protruded) a predetermined length from the distal portion of the catheter 14, the phase in the axial direction of the plurality of inner circumferential grooved portions 20 and the phase in the axial direction of the plurality of ridged and grooved portions 22 are shifted from each other.

The indwelling needle 12 including the piercing needle 10 according to the present embodiment is basically constructed as described above. Next, a method of using the indwelling needle 12 and operations and effects of the indwelling needle 12 will be described.

Figure 5:
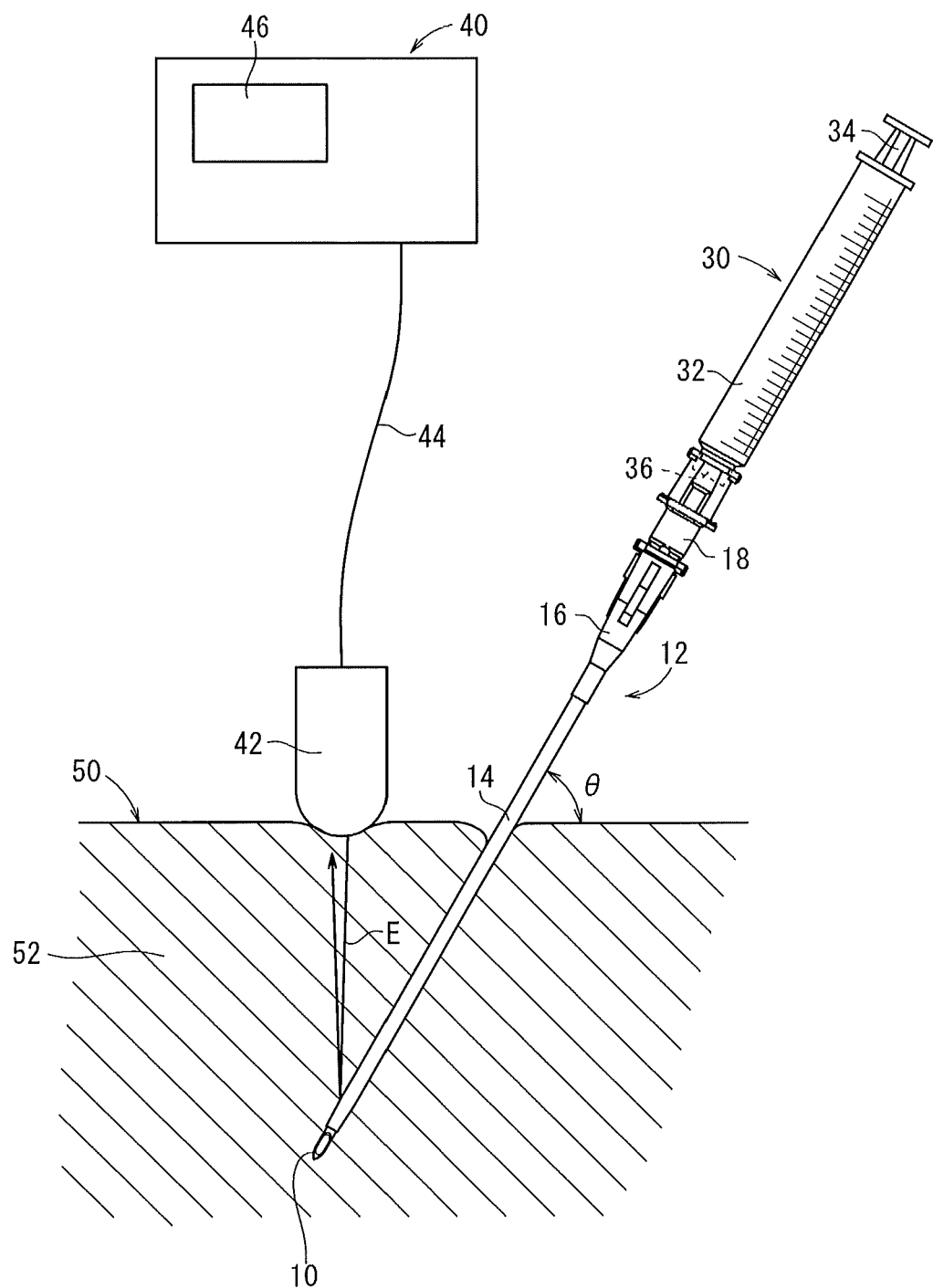
FIG. 5 is a schematic illustration showing the manner in which an indwelling needle, having an ultrasound-guided piercing needle according to one embodiment of the present invention, is made to pierce a patient while the ultrasound-guided piercing needle is detected by an ultrasonic imaging device.

Prior to piercing by the indwelling needle 12, a syringe 30 is connected to a proximal portion of an inner needle hub 18, as shown in FIG. 5. The syringe 30 includes a hollow cylindrical syringe main body 32, and a plunger 34 inserted inside the syringe main body 32. The syringe main body 32 is provided at a distal portion thereof with a connection port 36, which is connected to a proximal portion of the inner needle hub 18. Consequently, the syringe 30 communicates with the interior of the inner needle hub 18 through the connection port 36.

Figure 6:
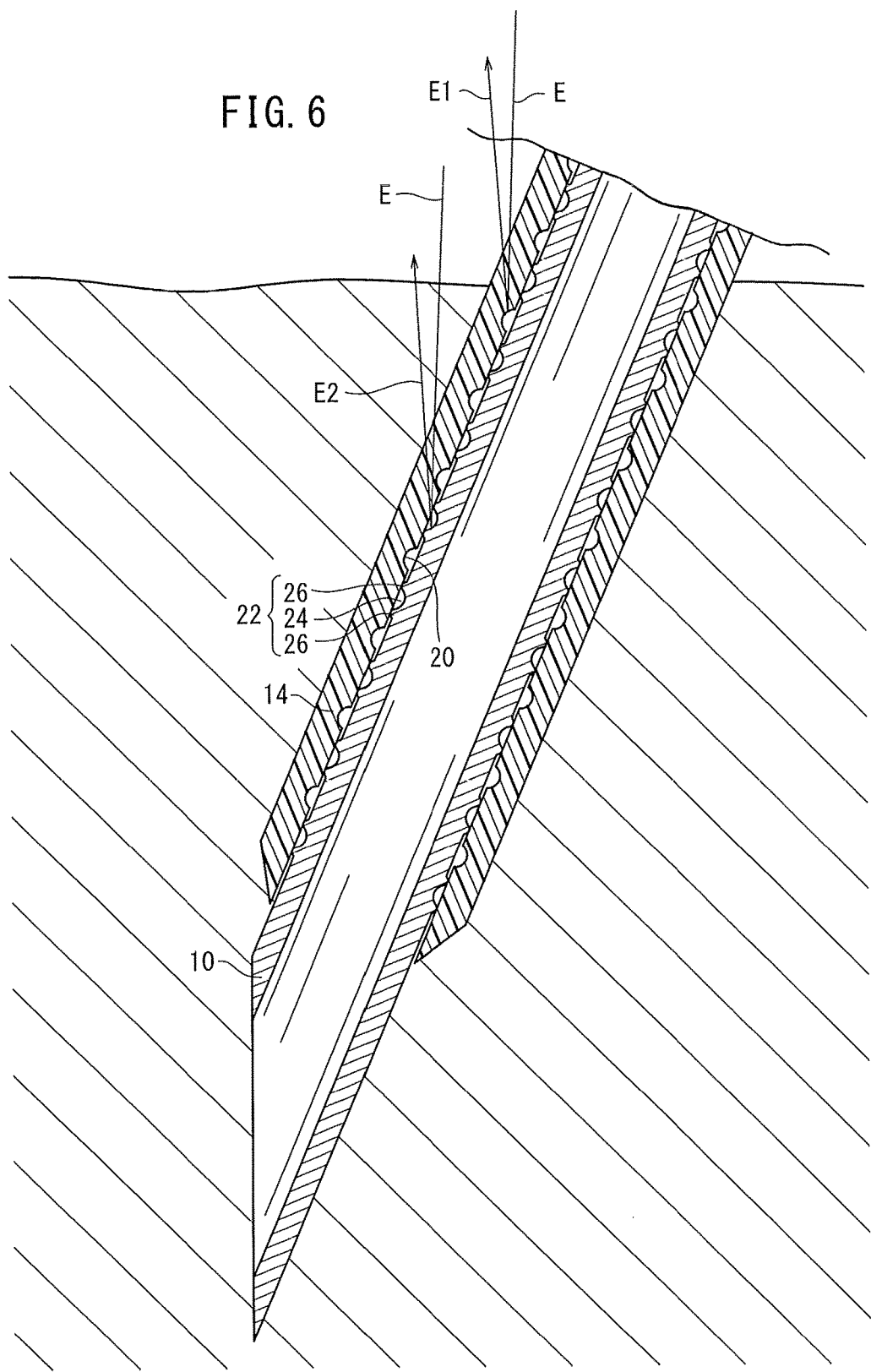
FIG. 6 is an enlarged schematic illustration of a condition in which ultrasonic waves, which are irradiated on an indwelling needle having an ultrasound-guided piercing needle according to one embodiment of the present invention, are reflected.

To perform piercing using the indwelling needle 12, first, as shown in FIG. 5, the indwelling needle 12 inclusive of the piercing needle 10 is gripped by a health care staff worker such as a doctor or the like, and is made to pierce a blood vessel (vein) of a patient 50. The piercing needle 10 is gradually inserted toward a desired area, whereupon the distal portion of the piercing needle 10 is advanced while cutting open a body tissue 52. In this case, as shown in FIG. 6, the piercing needle 10 is inserted into the interior of the catheter 14, and in this condition, the ridged and grooved portions 22 of the piercing needle 10 are located inside the catheter 14. Therefore, the indwelling needle 12 is allowed to pierce the patient while the ridged and grooved portions 22 of the piercing needle 10 are prevented from coming into contact with the body tissue 52.

On the other hand, simultaneously with piercing of the patient by the indwelling needle 12, a probe 42 of an ultrasonic imaging device 40 is pressed onto the vicinity of the pierced part of the patient 50, and irradiation of the patient with an echo beam (ultrasonic waves) E is conducted. Incidentally, the probe 42 is configured so as to be capable of emitting the echo beam E as well as receiving reflected waves (a reflected echo) of the echo beam E.

The echo beam E is emitted in the direction from a skin surface toward the inside of the patient 50, and a distal portion of the indwelling needle 12 is irradiated with the echo beam E. Then, as shown in FIG. 6, the echo beam E is reflected toward the side of the probe 42 from inner wall surfaces of the inner circumferential grooved portions 20, which are formed at the inner circumferential surface of the catheter 14. Similarly, the echo beam E is reflected by air that is sealed inside the inner circumferential grooved portions 20. Ultrasonic waves (reflected waves) reflected by the inner circumferential grooved portions 20 are represented as a reflection echo E1. In this case, the reflection echo E1, which is reflected by the inner wall surfaces of the inner circumferential grooved portions 20, is not attenuated by air that exists in the inner circumferential grooved portions 20. Therefore, the reflection echo E1 has an intensity approximately equal to the intensity of the emitted echo beam E. The reflection echo E1 is received by the probe 42.

In addition, the echo beam E is transmitted through the catheter 14, so as to be reflected from the ridged and grooved portions 22 toward the side of the probe 42. Reflected waves reflected by the ridged and grooved portions 22 are represented as a reflection echo E2. The reflection echo E2, which is reflected by the ridged and grooved portions 22, includes a reflection component reflected by the grooved portion 24, and another reflection component reflected by the ridged portions 26. The reflection echo E2 reflected by the ridged and grooved portions 22 is received by the probe 42.

As mentioned above, in the present embodiment, the grooved portion 24 is arcuate in cross section and the inner wall surface thereof constitutes an arcuate reflecting surface. The ridged portions 26 are arcuate in cross section and outer wall surfaces thereof constitute arcuate reflecting surfaces. Therefore, even if the piercing angle θ (see FIG. 5) of the indwelling needle 12 changes, the echo beam E emitted from the probe 42 can be reflected by the inner wall surfaces of the grooved portions 24 as well as by the outer wall surfaces of the ridged portions 26 toward the side of the probe 42.

When reflected waves (reflection echoes E1, E2) of the echo beam E are received by the probe 42, data concerning the reception thereof is output from the probe 42 through lead wires 44 and is sent to a control unit (not shown) of the ultrasonic imaging device 40 in order to be processed and thereafter displayed as an image on a display unit 46. More specifically, an image of the catheter 14 and the piercing needle 10, which is displayed on the display unit 46, is displayed in a linear form as a length along the axial direction of the ridged and grooved portions 22, which have been detected by the ultrasonic imaging device 40. Consequently, whether or not the distal portion of the piercing needle 10 has reached the blood vessel (vein) of the patient 50 can be confirmed by observing the display unit 46.

As a result, the vicinity of the distal portion of the piercing needle 10 is clearly displayed as an image on the display unit 46 of the ultrasonic imaging device 40, whereby the position of the piercing needle 10 that makes up the indwelling needle 12 can be confirmed with high accuracy.

Then, the doctor or the like moves the piercing needle 10 and the probe 42 while observing the display unit 46, so as to guide the piercing needle 10 toward the blood vessel of the patient 50. In this instance, the indwelling needle 12 is advanced while the plunger 34 of the syringe 30 is withdrawn appropriately. When the piercing needle 10 has pierced the blood vessel correctly, blood is introduced through the connection port 36 of the syringe 30 into the syringe main body 32, resulting in flashback.

Once piercing of the blood vessel by the piercing needle 10 has been confirmed in this manner, the piercing needle 10 and the syringe 30 are removed, thereby leaving the catheter 14 and a guide wire (not shown) inserted in the blood vessel through the catheter 14, after which the catheter 14 is removed. Next, a central venous catheter (not shown) is placed along the guide wire in an indwelling state in the blood vessel. Subsequently, a transfusion line (not shown) is connected to a central arterial catheter, and pabulum, a medicinal liquid, or the like is supplied into the blood vessel.

At the time of evulsing the piercing needle 10 while leaving the catheter 14 behind, the piercing needle 10 is evulsed to the exterior of the patient's body through the interior (lumen) of the catheter 14, so that the ridged and grooved portions 22 of the piercing needle 10 are prevented from coming into contact with body tissue 52, in the same manner as when the patient is pierced with the piercing needle.

As described above, according to the piercing needle 10 of the present embodiment, the ridged and grooved portion 22 is composed of the grooved portion 24 and the ridged portions 26 provided on both sides of the grooved portion 24, such that ultrasonic waves are reflected not only at the grooved portion 24 but also on the ridged portions 26. Therefore, ultrasonic waves can be reflected assuredly and suitably, so as to be detected by the ultrasonic imaging device 40. As a result, the position of the piercing needle 10, which is made to pierce the patient, can be confirmed by the ultrasonic imaging device 40 assuredly and with high accuracy, whereby a safe and assured procedure can be carried out while confirming the position of the piercing needle 10.

In addition, in the present embodiment, the ridged and grooved portions 22 are disposed in an annular form. Therefore, the entire circumference of the ridged and grooved portions 22 constitutes a reflecting surface. Therefore, ultrasonic waves can be effectively reflected, irrespective of the position around the axis of the piercing needle 10 at the time of piercing. Further, since plural ridged and grooved portions 22 are provided along the axial direction of the piercing needle 10, the number of parts provided for suitable reflection of ultrasonic waves is increased. Therefore, ultrasonic waves can be reflected effectively, and more sufficient reflected waves can be obtained. Consequently, the position of the piercing needle 10 can be confirmed with higher accuracy by the ultrasonic imaging device 40.

Further, in the present embodiment, the grooved portion 24 is arcuate in cross section, and the inner wall surface thereof constitutes an arcuate reflecting surface. The ridged portions 26 are arcuate in cross section, and the outer wall surfaces thereof constitute arcuate reflecting surfaces. Therefore, even in the case that the piercing angle θ (see FIG. 5) of the indwelling needle 12 changes, ultrasonic waves emitted from the probe 42 can be reflected back toward the side of the probe 42 by the inner wall surface of the grooved portion 24 and the outer wall surfaces of the ridged portions 26. In other words, ultrasonic waves can be reflected toward the side of the probe 42, whereby the position of the indwelling needle 12 can be confirmed irrespective of the piercing angle θ of the indwelling needle 12.

Furthermore, the inner circumferential grooved portions 20 are formed on the inner circumferential surface of the catheter 14, so that ultrasonic waves also are reflected at the inner circumferential grooved portions 20. Therefore, the intensity of the reflected waves, which are received by the probe 42, can be enhanced, whereby a clearer echo image can be obtained. As a result, the position of a distal portion of the indwelling needle 12 can be confirmed with high accuracy.

Figure 7:
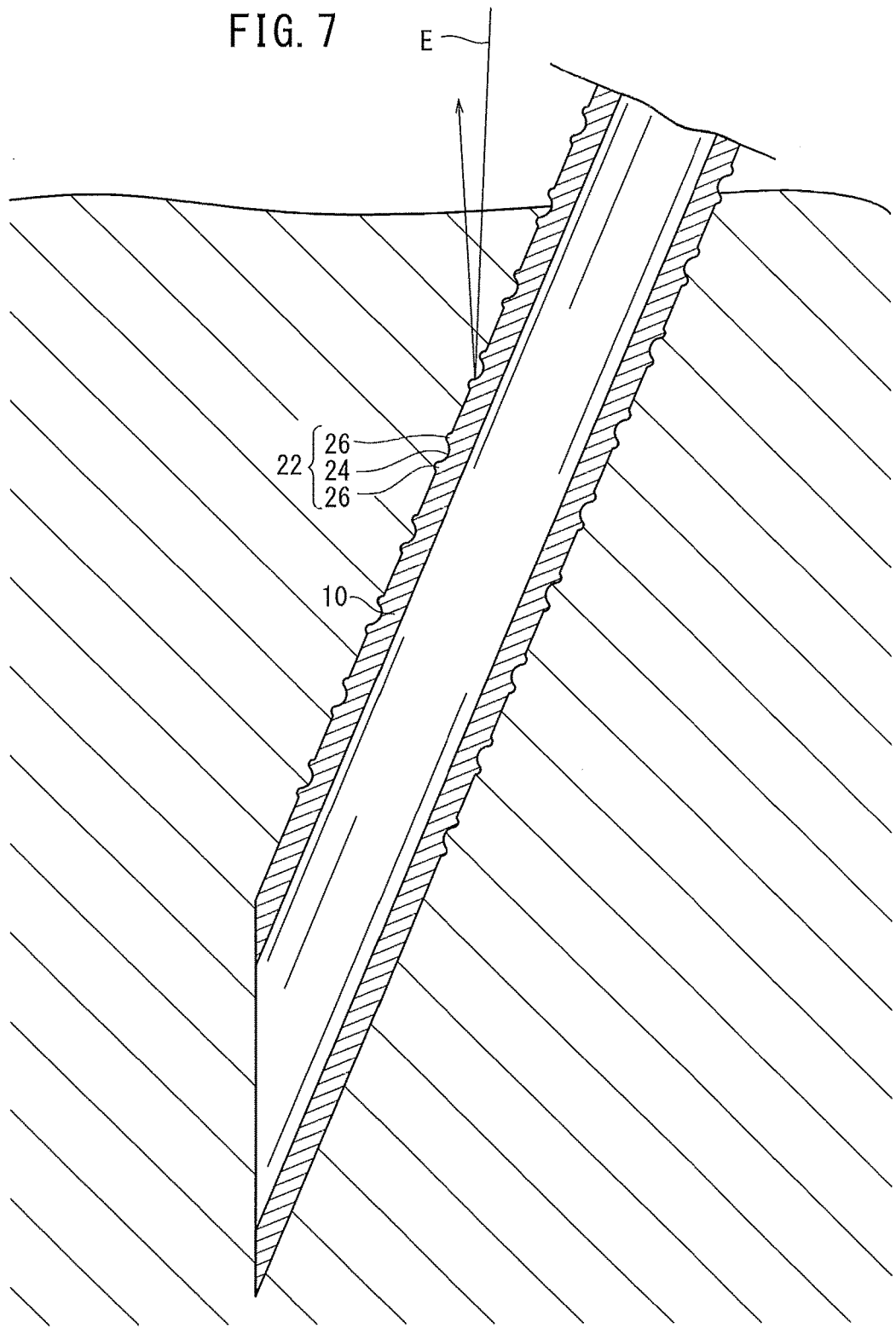
FIG. 7 is a schematic illustration of a mode of usage, in which an ultrasound-guided piercing needle according to one embodiment of the present invention is made to directly pierce a patient.

Incidentally, while a mode of use of the piercing needle 10 according to the present embodiment has been described above with reference to a case in which the piercing needle 10 is configured as an inner needle of an indwelling needle 12, which includes both an outer needle and the inner needle, the piercing needle 10 of the present invention also is applicable to cases in which the piercing needle 10 is made to directly pierce a patient to capture a blood vessel of the patient, without using a catheter 14, as shown in FIG. 7. In this case, for example, a Y hub (not shown) is connected to a proximal portion of the inner needle hub 18, and a guide wire and a central arterial catheter are passed through the Y hub, the inner needle hub 18, and the piercing needle 10. Thus, a procedure, which is the same or similar to the aforementioned procedure, can be carried out. Furthermore, in such a mode of use, ultrasonic waves (the echo beam E) can be reflected by the ridged and grooved portions 22 assuredly and suitably, and the position of the piercing needle 10, in a state of piercing the patient, can be confirmed by the ultrasonic imaging device 40 assuredly and with high accuracy, so that a safe and assured procedure can be carried out while confirming the position of the piercing needle 10.

In addition, while a mode of use of the piercing needle 10 according to the present embodiment has been described above with reference to a case in which the piercing needle 10 is used as a guide wire introducing needle in order to place a central arterial catheter in an indwelling state by a so-called Seldinger catheter technique, the piercing needle 10 of the present invention can also be used as an indwelling needle for performing a transfusion by being set in an indwelling manner in a deletion blood vessel. The piercing needle 10 can also be used as a biopsy needle for sampling a portion of a body tissue or cells, or the like.

Figure 8:
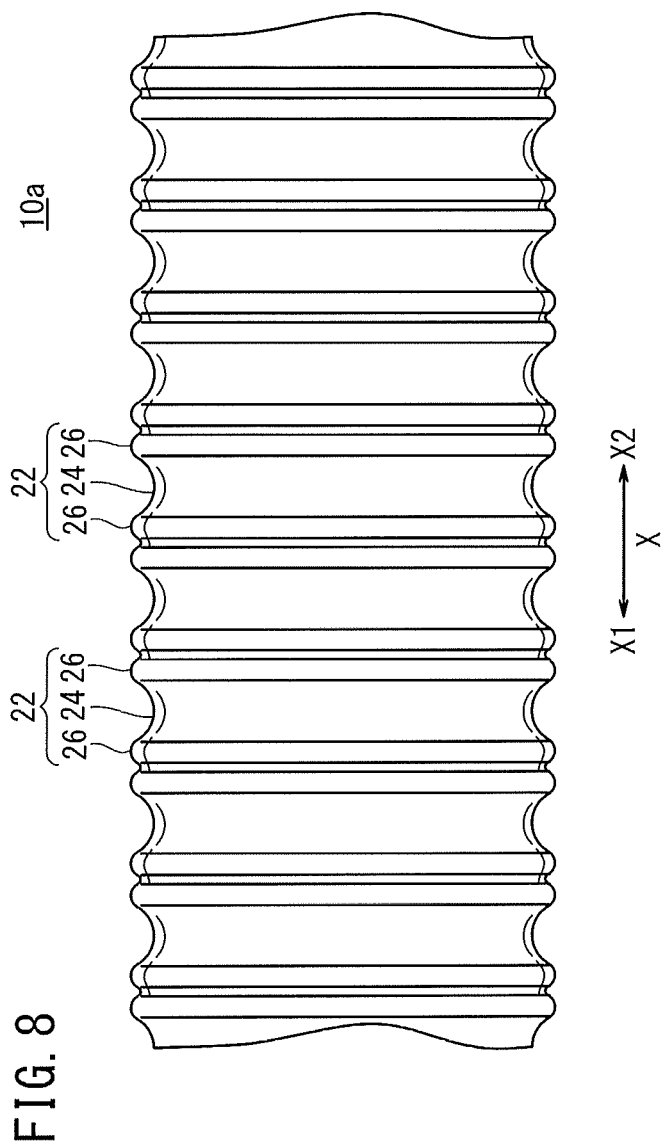
FIG. 8 is an enlarged side view showing grooved portions of an ultrasound-guided piercing needle according to a first modification.

FIG. 8 is a side view showing the configuration of a distal portion, and portions in the vicinity thereof, of an ultrasound-guided piercing needle 10a (hereinafter referred to simply as a "piercing needle 10a") according to a first modification. In the piercing needle 10a according to the first modification, plural ridged and grooved portions 22 may be formed such that ridged portions 26 of the adjacent ridged and grooved portions 22 are continuous (connected) with each other. By the ridged and grooved portions 22 of the piercing needle 10 being formed in this manner, the amount of reflected waves directed toward the side of the probe 42 can be increased, compared with the case of the piercing needle 10 according to the basic form thereof, as described above in relation to the aforementioned embodiment. As a result, confirmation of the position of the piercing needle 10a by the ultrasonic imaging device 40 can be performed with higher accuracy.

FIG. 9 is a side view showing the configuration of a distal portion, and portions in the vicinity thereof, of an ultrasound-guided piercing needle 10b (hereinafter referred to simply as a "piercing needle 10b") according to a second modification. In the piercing needle 10b according to the second modification, a ridged and grooved portion 27 having a grooved portion 28 and ridged portions 29 on both sides of the grooved portion 28 may be formed in a helical shape, which extends in the axial direction of the piercing needle 10b, while also extending around the outer circumferential surface of the piercing needle 10b at least a plurality of times. By configuring the ridged and grooved portion 27 in this manner, ultrasonic waves can be effectively reflected, and more sufficient reflected waves can be obtained, similar to the case of the ridged and grooved portions 22 described above. Consequently, confirmation of the position of the piercing needle 10b by the ultrasonic imaging device 40 can be performed with enhanced accuracy.

In addition, by forming the ridged and grooved portion 27 of the piercing needle 10b in a helical shape, when the piercing needle 10b is inserted into the catheter 14, it is ensured that the phase in the axial direction of the plurality of inner circumferential grooved portions 20, and the phase in the axial direction of the ridged and grooved portion 27 can easily be shifted from each other.

Further, the inner circumferential grooved portion 20 of the catheter 14 may be formed in a helical shape having a different angle from that of the ridged and grooved portion 27, or alternatively, the inner circumferential grooved portion 20 of the catheter 14 may be formed in a helical shape in a different direction from that of the ridged and grooved portion 27. With such a configuration as well, the phase in the axial direction of the inner circumferential grooved portion 20, and the phase in the axial direction of the ridged and grooved portion 27 can easily be shifted from each other.

When the phase in the axial direction of the inner circumferential grooved portion(s) 20, and the phase in the axial direction of the ridged and grooved portion(s) 27 are shifted from each other, attenuation in the intensity of the reflected ultrasonic waves can be restrained.

Incidentally, the present invention is not restricted to the above-described embodiments, and naturally, various configurations are possible without deviating from the gist of the invention.

The invention claimed is:

1. An ultrasound-guided piercing needle having an annular ridged and grooved portion, which reflects ultrasonic waves, the ridged and grooved portion comprising:
    an annular grooved portion provided in an outer circumferential surface of a needle body near a distal portion having a blade face; and
    annular ridged portions provided on both sides of the grooved portion in an axial direction of the needle body, an outer diameter of the ridged portions being greater than an outer diameter of the outer circumferential surface of the needle body;
    wherein the annular ridged portions are arcuate in cross section and formed with a substantially constant height over a circumferential direction.

2. The ultrasound-guided piercing needle according to claim 1, wherein a plurality of annular ridged and grooved portions are provided along an axial direction of the ultrasound-guided piercing needle.

3. The ultrasound-guided piercing needle according to claim 2, wherein the plurality of annular ridged and grooved portions are formed such that the ridged portions of adjacent ridged and grooved portions are continuous with each other.

4. The ultrasound-guided piercing needle according to claim 1, wherein the annular ridged and grooved portion is formed in a helical shape extending around the outer circumferential surface at least a plurality of times.

5. The ultrasound-guided piercing needle according to claim 1, wherein the grooved portion is arcuate in cross section.

6. The ultrasound-guided piercing needle according to claim 5, wherein the grooved portion and the ridged portions form a continuous curve in cross section.

7. The ultrasound-guided piercing needle according to claim 5, wherein the grooved portion has a depth in a radial direction in a range from 5 to 20 µm, and the ridged portions have a height in a radial direction in a range from 1 to 15 µm.

8. The ultrasound-guided piercing needle according to claim 1, wherein the annular grooved portion is formed in a helical shape extending around the outer circumferential surface at least a plurality of times.

9. The ultrasound-guided piercing needle according to claim 1, wherein the annular ridged portions are formed in a helical shape extending around the outer circumferential surface at least a plurality of times.

10. The ultrasound-guided piercing needle according to claim 1, wherein the annular ridged and grooved portion extends a first axial length, an axial length of the needle body between a first said annular ridged and grooved portion and a second said annular ridged and grooved portion being greater than the first axial length.

11. The ultrasound-guided piercing needle according to claim 1, wherein the needle body comprises a hollow needle body;
    wherein a depth of the grooved portion relative to an outside diameter of the hollow needle body defines a first height;
    wherein an outer diameter of the ridged portions relative to the outside diameter of the hollow needle body defines a second height;
    wherein a wall thickness of the hollow needle body at a location of the grooved portion is defined by the outside diameter of the hollow needle body less an inside diameter of the hollow needle body and less the first height; and
    wherein the wall thickness of the hollow needle body at the location of the grooved portion is greater than the first height plus the second height.

12. An indwelling needle comprising an inner needle and an outer needle in which the inner needle is inserted, wherein the inner needle is configured as an ultrasound-guided piercing needle having a ridged and grooved portion, which reflects ultrasonic waves; and
    the ridged and grooved portion further comprises:
    an annular grooved portion provided in an outer circumferential surface of a needle body near a distal portion having a blade face; and
    annular ridged portions provided on both sides of the grooved portion in an axial direction of the needle body, an outer diameter of the ridged portions being greater than an outer diameter of the outer circumferential surface of the needle body;
    wherein the annular ridged portions are arcuate in cross section and formed with a substantially constant height over a circumferential direction.

13. The indwelling needle according to claim 12, wherein the outer needle has a catheter and an outer needle hub connected to a proximal portion of the catheter,
    a proximal portion of the inner needle has an inner needle hub, and
    an inner circumferential surface of the catheter has an inner circumferential grooved portion that is hollowed toward an outer circumference in a vicinity of a distal portion of the catheter.

14. The indwelling needle according to claim 13, wherein the inner circumferential grooved portion of the catheter is substantially semicircular in cross section, and has an annular shape with substantially constant depth in a circumferential direction, and
    the inner circumferential grooved portion is formed in plural at predetermined intervals in an axial direction over a predetermined range.

15. The indwelling needle according to claim 13, wherein the inner needle hub is configured to fit into an interior of the outer needle hub,
    the inner circumferential grooved portion of the catheter and the ridged and grooved portion of the inner needle are shifted from each other in an axial direction in a state where the inner needle hub fits into the interior of the outer needle hub.

16. The indwelling needle according to claim 12, wherein the annular grooved portion is formed in a helical shape extending around the outer circumferential surface at least a plurality of times.

17. The indwelling needle according to claim 12, wherein the annular ridged portions are formed in a helical shape extending around the outer circumferential surface at least a plurality of times.

18. The indwelling needle according to claim 12, wherein the annular ridged and grooved portion extends a first axial length, an axial length of the needle body between a first said annular ridged and grooved portion and a second said annular ridged and grooved portion being greater than the first axial length.

19. An ultrasound-guided piercing needle having an annular ridged and grooved portion which reflects ultrasonic waves, the ridged and grooved portion comprising:

an annular grooved portion provided in an outer circumferential surface of a needle body near a distal portion having a blade face; and annular ridged portions provided on both sides of the grooved portion in an axial direction of the needle body, an outer diameter of the ridged portions being greater than an outer diameter of the outer circumferential surface of the needle body;

wherein the annular ridged and grooved portion extends a first axial length, an axial length of the needle body between a first said annular ridged and grooved portion and a second, closes said annular ridged and grooved portion being greater than the first axial length.

\* \* \* \* \*